(12) United States Patent
Ikeda et al.

(10) Patent No.: US 7,524,667 B2
(45) Date of Patent: Apr. 28, 2009

(54) MUTATED 6-PHOSPHOGLUCONATE DEHYDROGENASE

(75) Inventors: Masato Ikeda, Nagano (JP); Junko Ohnishi, Nagano (JP); Satoshi Mitsuhashi, Hofu (JP); Keiko Ochiai, Ebina (JP)

(73) Assignee: Kyowa Hakko Food Specialties Co., Ltd., Yamaguchi (JP)

( * ) Notice: Subject to any disclaimer, the term of this patent is extended or adjusted under 35 U.S.C. 154(b) by 241 days.

(21) Appl. No.: 10/497,502

(22) PCT Filed: Dec. 3, 2002

(86) PCT No.: PCT/JP02/12661

§ 371 (c)(1),
(2), (4) Date: Jun. 3, 2004

(87) PCT Pub. No.: WO03/048351

PCT Pub. Date: Jun. 12, 2003

(65) Prior Publication Data

US 2005/0079586 A1 Apr. 14, 2005

(30) Foreign Application Priority Data

Dec. 3, 2001 (JP) ............................. 2001-368264

(51) Int. Cl.
*C12N 9/04* (2006.01)
*C12N 1/20* (2006.01)
*C12N 15/00* (2006.01)
*C12Q 1/00* (2006.01)
*C12Q 1/68* (2006.01)
*C12P 21/04* (2006.01)
*C07H 21/04* (2006.01)

(52) U.S. Cl. .............................. 435/190; 435/4; 435/6; 435/69.1; 435/71.1; 435/440; 435/252.3; 435/320.1; 536/23.2

(58) Field of Classification Search ....................... None
See application file for complete search history.

(56) References Cited

U.S. PATENT DOCUMENTS 5,830,716 A   11/1998   Kojima et al.
6,162,618 A * 12/2000   Warren ...................... 435/69.1
7,141,664 B2 * 11/2006   Zelder et al. ............... 536/23.7

FOREIGN PATENT DOCUMENTS

EP   1108790    6/2001
EP   1 227 152  7/2002
JP   9-224662   9/1997
WO   00/34484   6/2000
WO   01/04325   1/2001

OTHER PUBLICATIONS

Branden et al. (introduction to Protein Structure, Garland Publishing Inc., New York, p. 247, 1991.*
Cerdeno-Tarraga et al. NCBI Database, Accession No. Q6NHC5, 2006.*
Nishio et al. NCBI Database, Accession No. Q8FTL1, 2006.*
Tauch et al. NCBI Database, Accession No. Q4JVT1, 2006.*
Supplementary Partial European Search Report, for Application No. EP 02 78 1875, dated Feb. 24, 2006.
A. Marx, et al., "Response of the Central Metabolism of *Corynebecterium glutamicum* to Different Flux Burdens", *Biotechnology and Bioengineering*, vol. 56, No. 2, Oct. 20, 1997, pp. 168-180.
J. Ohnishi, et al., A novel gnd mutation leading to increased L-lysine production in *Corynebacterium glutamicum*, FEMS Microbiology Letters, vol. 242 (Jan. 15, 2005), pp. 265-274.
Nature, Complete genome sequence of the model actinomycete *Strepto coelicolor* A3(2), vol. 417 (XP-002366709), Dec. 1, 2001, pp. 141-147.
Sugimoto, et al., "Regulation of 6-Phosphogluconate Dehydrogenase in *Brevibacterium flavum*", Agric. Biol. Chem., 51 (5), 1257-1263, 1987.
Moritz, et al., "Kinetic properties of the glucose-6-phosphate and 6-phosphogluconate dehydrogenases from *Corynebacterium glutamicum* and their application for predicting pentose phosphate pathway flux in vivo", Eur. J. Biochem. 267, 3442-3452, 2000.
Bianchi, et al., " Effect of gluconic acid as a secondary carbon source on non-growing L-lyside producers cells of *Corynebacterium glutamicum*. Purification and properties of 6-phosphogluconate dehydrogenase", Enzyme and Microbial Technology, 28 (2001), 754-759.

* cited by examiner

*Primary Examiner*—Yong D Pak
(74) *Attorney, Agent, or Firm*—Antonelli, Terry, Stout & Kraus, LLP.

(57) ABSTRACT

The present invention relates to a polypeptide having a modified amino acid sequence of 6-phosphogluconate dehydrogenase (hereinafter abbreviated as GND) derived from a microorganism belonging to the genus *Corynebacterium*, said modification being substitution of the amino acid residue(s) at the position(s) corresponding to the 158th and/or the 361st amino acid(s) of the amino acid sequence shown in SEQ ID NO: 1, and having GND activity; DNA encoding the polypeptide; a recombinant DNA comprising the DNA; a transformant carrying the recombinant DNA; a microorganism carrying the DNA on the chromosome; and a process for producing a useful substance which comprises culturing the transformant or the microorganism in a medium.

5 Claims, No Drawings

US 7,524,667 B2

MUTATED 6-PHOSPHOGLUCONATE DEHYDROGENASE

TECHNICAL FIELD

The present invention relates to a polypeptide having 6-phosphogluconate dehydrogenase (hereinafter abbreviated as GND) activity, DNA encoding the polypeptide, a recombinant DNA comprising the DNA, a transformant carrying the recombinant DNA, a microorganism carrying the DNA on the chromosome, and a process for producing a useful substance which comprises culturing the transformant or the microorganism in a medium.

BACKGROUND ART

GND, which is one of the enzymes in the pentose phosphate cycle, oxidizes and decarboxylates 6-phosphogluconic acid to form D-ribulose-5-phosphate.

As the DNAs encoding GND, those derived from *Escherichia coli* [Gene, 27, 253 (1984)], *Bacillus subtilis* [J. Biol. Chem., 261, 13744 (1986)], etc. have been isolated and their nucleotide sequences have been reported.

With regard to microorganisms belonging to the genus *Corynebacterium*, there are reports on GND of *Corynebacterium glutamicum* disclosing the biochemical properties and the nucleotide sequences of genes encoding GND [Agric. Biol. Chem., 51, 1257 (1987); Eur. J. Biochem., 267, 3442 (2000); Enzyme Microb. Technol., 28, 754 (2001); Japanese Published Unexamined Patent Application No. 224662/97; EP1108790].

However, it is not known yet that introduction of a mutation into DNA encoding GND can enhance the productivity of metabolites. Further, there is no report that describes or suggests what mutation should be introduced into DNA encoding GND to obtain the above effect.

DISCLOSURE OF THE INVENTION

An object of the present invention is to provide a novel mutant GND, DNA encoding the enzyme, a recombinant DNA comprising the DNA, a transformant carrying the recombinant DNA, a microorganism carrying the DNA on the chromosome, or a process for producing a useful substance by using the transformant or the microorganism.

The present invention relates to the following (1) to (23).

(1) A polypeptide selected from the group consisting of polypeptides according to the following (a) to (f):

(a) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, and having GND activity;

(b) a polypeptide having a modified amino acid sequence of GND derived from a microorganism belonging to the genus *Corynebacterium*, said modification being substitution of the amino acid residue at the position corresponding to the 361st amino acid of the amino acid sequence shown in SEQ ID NO: 1 by an amino acid residue different from a Ser residue, and having GND activity;

(c) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue and substitution of the amino acid residue at the position corresponding to the 361st amino acid of the amino acid sequence shown in SEQ ID NO: 1 by an amino acid residue different from a Ser residue, and having GND activity;

(d) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, and deletion, substitution or addition of one or more amino acid residues different from the amino acid residue at the substituted position, and having GND activity;

(e) a polypeptide having a modified amino acid sequence of GND derived from a microorganism belonging to the genus *Corynebacterium*, said modification being substitution of the amino acid residue at the position corresponding to the 361st amino acid of the amino acid sequence shown in SEQ ID NO: 1 by an amino acid residue different from a Ser residue, and deletion, substitution or addition of one or more amino acid residues different from the amino acid residue at the substituted position, and having GND activity; and (f) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, substitution of the amino acid residue at the position corresponding to the 361st amino acid of the amino acid sequence shown in SEQ ID NO: 1 by an amino acid residue different from a Ser residue, and deletion, substitution or addition of one or more amino acid residues different from the amino acid residues at the substituted positions, and having GND activity.

(2) The polypeptide according to the above (1), wherein the GND derived from a microorganism belonging to the genus *Corynebacterium* is GND having the amino acid sequence shown in SEQ ID NO: 1.

(3) The polypeptide according to the above (1) or (2), wherein the amino acid residue different from a Pro residue is a Ser residue.

(4) The polypeptide according to the above (1) or (2), wherein the amino acid residue different from a Ser residue is a Phe residue.

(5) The polypeptide according to the above (1) or (2), wherein the amino acid residue different from a Pro residue is a Ser residue and the amino acid residue different from a Ser residue is a Phe residue.

(6) A DNA encoding the polypeptide according to any of the above (1) to (5).

(7) A DNA selected from the group consisting of DNAs according to the following (a) to (f):

(a) DNA having a modified nucleotide sequence of DNA encoding GND derived from a microorganism belonging to the genus *Corynebacterium*, said modification being substitution of the region corresponding to the nucleotide sequence at positions 472 to 474 of the nucleotide sequence shown in SEQ ID NO: 2 by a codon encoding an amino acid residue different from a Pro residue, and encoding a polypeptide having GND activity;

(b) DNA having a modified nucleotide sequence of DNA encoding GND derived from a microorganism belonging to the genus *Corynebacterium*, said modification being substitution of the region corresponding to the nucleotide sequence at positions 1081 to 1083 of the nucleotide sequence shown in SEQ ID NO: 2 by a codon encoding an amino acid residue different from a Ser residue, and encoding a polypeptide having GND activity;

(c) DNA having a modified nucleotide sequence of DNA encoding GND derived from a microorganism belonging to the genus *Corynebacterium*, said modification being substitution of the region corresponding to the nucleotide sequence at positions 472 to 474 of the nucleotide sequence shown in SEQ ID NO: 2 by a codon encoding an amino acid residue different from a Pro residue and substitution of the region corresponding to the nucleotide sequence at positions 1081 to 1083 of the nucleotide sequence shown in SEQ ID NO: 2 by a codon encoding an amino acid residue different from a Ser residue, and encoding a polypeptide having GND activity;

(d) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 472 to 474 of the nucleotide sequence shown in SEQ ID NO: 2 by a codon encoding an amino acid residue different from a Pro residue, having a codon encoding an amino acid residue different from a Pro residue at the region corresponding to said substituted region, and encoding a polypeptide having GND activity;

(e) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 1081 to 1083 of the nucleotide sequence shown in SEQ ID NO: 2 by a codon encoding an amino acid residue different from a Ser residue, having a codon encoding an amino acid residue different from a Ser residue at the region corresponding to said substituted region, and encoding a polypeptide having GND activity; and (f) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 472 to 474 of the nucleotide sequence shown in SEQ ID NO: 2 by a codon encoding an amino acid residue different from a Pro residue and substitution of the region corresponding to the nucleotide sequence at positions 1081 to 1083 of the nucleotide sequence shown in SEQ ID NO: 2 by a codon encoding an amino acid residue different from a Ser residue, having codons encoding an amino acid residue different from a Pro residue and an amino acid residue different from a Ser residue at the regions corresponding to said substituted regions, respectively, and encoding a polypeptide having GND activity.

(8) The DNA according to the above (7), wherein the DNA encoding GND derived from a microorganism belonging to the genus *Corynebacterium* is DNA having the nucleotide sequence shown in SEQ ID NO: 2.

(9) The DNA according to the above (7) or (8), wherein the codon encoding an amino acid residue different from a Pro residue is a codon encoding a Ser residue.

(10) The DNA according to the above (7) or (8), wherein the codon encoding an amino acid residue different from a Ser residue is a codon encoding a Phe residue.

(11) The DNA according to the above (7) or (8), wherein the codon encoding an amino acid residue different from a Pro residue is a codon encoding a Ser residue and the codon encoding an amino acid residue different from a Ser residue is a codon encoding a Phe residue.

(12) A recombinant DNA comprising the DNA according to any of the above (6) to (11).

(13) A transformant carrying the recombinant DNA according to the above (12).

(14) The transformant according to the above (13), which is a microorganism selected from the group consisting of microorganisms belonging to the genera *Corynebacterium, Brevibacterium* and *Microbacterium*.

(15) The transformant according to the above (13) or (14), which is a microorganism belonging to *Corynebacterium glutamicum*.

(16) A microorganism carrying the nucleotide sequence of the DNA according to any of the above (6) to (11) on the chromosome.

(17) The microorganism according to the above (16), which is selected from the group consisting of microorganisms belonging to the genera *Corynebacterium, Brevibacterium* and *Microbacterium*.

(18) The microorganism according to the above (16) or (17), which belongs to *Corynebacterium glutamicum*.

(19) A process for producing a useful substance which comprises culturing the transformant or microorganism according to any of the above (13) to (18) in a medium, allowing the useful substance to form and accumulate in the culture, and recovering the useful substance from the culture.

(20) The process according to the above (19), wherein the useful substance is an L-amino acid, a nucleic acid or its derivative, a carbohydrate or a vitamin.

(21) The process according to the above (19) or (20), wherein the useful substance is a substance synthesized via the pentose phosphate cycle or biosynthesized using NADPH.

(22) The process according to any of the above (19) to (21), wherein the useful substance is an L-amino acid, or a nucleic acid or its derivative.

(23) The process according to any of the above (19) to (22), wherein the useful substance is an L-amino acid selected from the group consisting of L-lysine, L-threonine, L-isoleucine, L-arginine, L-phenvlalanine, L-tyrosine and L-tryptophan.

The present invention is described in detail below.

BEST MODES FOR CARRYING OUT THE INVENTION (1) Polypeptide of the Present Invention The polypeptides of the present invention include a polypeptide selected from the group consisting of polypeptides according to the following (a) to (c):

(a) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, and having GND activity;

(b) a polypeptide having a modified amino acid sequence of GND derived from a microorganism belonging to the genus *Corynebacterium*, said modification being substitution of the amino acid residue at the position corresponding to the 361st amino acid of the amino acid sequence shown in SEQ ID NO: 1 by an amino acid residue different from a Ser residue, and having GND activity; and (c) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue and substitution of the amino acid residue at the position corresponding to the 361st amino acid of the amino acid sequence shown in SEQ ID NO: 1 by an amino acid residue different from a Ser residue, and having GND activity.

Examples of the microorganisms belonging to the genus *Corynebacterium* are *Corynebacterium acetoacidophilum*, *Corynebacterium acetoglutamicum*, *Corynebacterium callunae*, *Corynebacterium glutamicum*, *Corynebacterium lactofermentum*, *Corynebacterium herculis*, *Corynebacterium lilium*, *Corynebacterium melassecola*, *Corynebacterium thermoaminogenes*, *Corynebacterium efficiens* and *Corynebacterium ammoniagenes*.

The GND derived from a microorganism belonging to the genus *Corynebacterim* may be any of the GND derived from the above microorganisms belonging to the genus *Corynebacterium*.

An example of the GND is GND having the amino acid sequence shown in SEQ ID NO: 1 described in EP1108790.

The above "amino acid residue at the position corresponding to the 158th amino acid of the amino acid sequence shown in SEQ ID NO: 1 in an amino acid sequence of GND derived from a microorganism belonging to the *Corynebacterium*" refers to the amino acid residue located at the position corresponding to the 158th amino acid of the amino acid sequence shown in SEQ ID NO: 1 in an amino acid sequence of GND derived from a microorganism belonging to the genus *Corynebacterium* when the amino acid sequence of GND derived from a microorganism belonging to the genus *Corynebacterium* and the amino acid sequence shown in SEQ ID NO: 1 are compared and aligned in such a way that the homology between them becomes highest as calculated by use of BLAST [J. Mol. Biol., 215, 403 (1990)], FASTA [Methods in Enzymology, 183, 63-98 (1990)], etc. The amino acid residue at the position corresponding to the 361st amino acid of the amino acid sequence shown in SEQ ID NO: 1 can also be determined in the same manner.

Any amino acid residue different from a Pro residue can be substituted for the amino acid residue at the position corresponding to the 158th amino acid of the amino acid sequence shown in SEQ ID NO: 1. Preferred amino acid residues are those having a neutral polar side chain such as Ser, Thr, Trp, Cys, Asn, Gln and Tyr. More preferred are those having a hydroxyl group on the side chain such as Ser and Thr, and a Ser residue is particularly preferred.

Any amino acid residue different from a Ser residue can be substituted for the amino acid residue at the position corresponding to the 361st amino acid of the amino acid sequence shown in SEQ ID NO: 1. Preferred amino acid residues are those having a nonpolar side chain such as Phe, Val, Leu, Ile, Met, Gly, Ala and Pro, and those having a ring-like structure on the side chain such as Phe and Trp. Particularly preferred is a Phe residue.

The polypeptides of the present invention further include polypeptides according to the following (d) to (f):

(d) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, and deletion, substitution or addition of one or more amino acid residues different from the amino acid residue at the substituted position, and having GND activity;

(e) a polypeptide having a modified amino acid sequence of GND derived from a microorganism belonging to the genus *Corynebacterium*, said modification being substitution of the amino acid residue at the position corresponding to the 361st amino acid of the amino acid sequence shown in SEQ ID NO: 1 by an amino acid residue different from a Ser residue, and deletion, substitution or addition of one or more amino acid residues different from the amino acid residue at the substituted position, and having GND activity; and (f) a polypeptide having a modified amino acid sequence of GND derived from a microorganism belonging to the genus *Corynebacterium*, said modification being substitution of the amino acid residue at the position corresponding to the 158th amino acid of the amino acid sequence shown in SEQ ID NO: 1 by an amino acid residue different from a Pro residue, substitution of the amino acid residue at the position corresponding to the 361st amino acid of the amino acid sequence shown in SEQ ID NO: 1 by an amino acid residue different from a Ser residue, and deletion, substitution or addition of one or more amino acid residues different from the amino acid residues at the substituted positions, and having GND activity.

The polypeptides according to the above (d) to (f) can be obtained by the same method as those of the above (a) to (c). The amino acid residues to be substituted can be determined by the same method as in the case of the polypeptide of the above (a) to (c).

The number of amino acid residues which are deleted, substituted or added is not specifically limited, but is within the range where deletion, substitution or addition is possible by known methods such as the above site-directed mutagenesis. The suitable number is 1 to dozens, preferably 1 to 20, more preferably 1 to 10, further preferably 1 to 5.

In order that the polypeptide of the present invention may have GND activity, it is desirable that the homology of its amino acid sequence to the amino acid sequence according to any of the above (a) to (c) is at least 60% or more, usually 80% or more, and particularly 95% or more, as calculated by use of BLAST, FASTA, etc.

The GND activity of the polypeptide of the present invention may be decreased, increased or the same, compared with that before the amino acid substitution. When it is decreased compared with that before the substitution, it is preferably 10% or more, more preferably 30% or more of the GND activity of GND having the amino acid sequence shown in SEQ ID NO: 1.

GND activity can be measured by known methods, for example, those described in Agric. Biol. Chem., 51, 1257 (1987), Enzyme Microb. Technol., 28, 754 (2001), etc.

Specifically, the GND activity of enzyme sources (e.g., a culture obtained by culturing the transformant of the present invention described hereinbelow in (3) or the microorganism described hereinbelow in (4), cells obtained from the culture, a cell-free extract obtained from the cells, and the polypeptide of the present invention purified from the cell-free extract) can be measured by performing reaction using a reaction mixture comprising 50 mmol/l Tris/HCl (pH 7.5) containing the enzyme source, 0.5 mmol/l NADP, 10 mmol/l $MgCl_2$ and 2 mmol/l 6-phosphogluconic acid at 30° C., measuring the increase in the absorbance at 340 nm, and determining the formed NADPH.

The above polypeptides of the present invention can be obtained by introducing a site-directed mutation into DNA encoding GND derived from a microorganism belonging to the genus *Corynebacterium* by site-directed mutagenesis described in Molecular Cloning: A Laboratory Manual, 3rd ed., Cold Spring Harbor Laboratory Press (2001) (hereinafter abbreviated as Molecular Cloning, 3rd ed.); Current Protocols in Molecular Biology, John Wiley & Sons (1987-1997) (hereinafter abbreviated as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

An example of the DNA encoding GND derived from the genus *Corynebacterium* is DNA having the nucleotide sequence shown in SEQ ID NO: 2 described in EP1108790.

When GND derived from a microorganism belonging to the genus *Corynebacterium* has a sequence wherein the amino acid residue corresponding to the 158 amino acid residue of the amino acid sequence shown in SEQ ID NO: 1 is an amino acid residue different from a Pro residue and the amino acid residue corresponding to the $361^{st}$ amino acid residue of the amino acid sequence shown in SEQ ID NO: 1 is an amino acid residue different from a Ser residue, the substitution does not necessarily have to be carried out.

(2) DNA of the Present Invention

The DNAs of the present invention encode the above polypeptides of the present invention.

The DNAs include those according to the following (a) to (c):

(a) DNA having a modified nucleotide sequence of DNA encoding GND derived from a microorganism belonging to the genus *Corynebacterium*, said modification being substitution of the region corresponding to the nucleotide sequence at positions 472 to 474 of the nucleotide sequence shown in SEQ ID NO: 2 by a codon encoding an amino acid residue different from a Pro residue, and encoding a polypeptide having GND activity;

(b) DNA having a modified nucleotide sequence of DNA encoding GND derived from a microorganism belonging to the genus *Corynebacterium*, said modification being substitution of the region corresponding to the nucleotide sequence at positions 1081 to 1083 of the nucleotide sequence shown in SEQ ID NO: 2 by a codon encoding an amino acid residue different from a Ser residue, and encoding a polypeptide having GND activity; and (c) DNA having a modified nucleotide sequence of DNA encoding GND derived from a microorganism belonging to the genus *Corynebacterium*, said modification being substitution of the region corresponding to the nucleotide sequence at positions 472 to 474 of the nucleotide sequence shown in SEQ ID NO: 2 by a codon encoding an amino acid residue different from a Pro residue and substitution of the region corresponding to the nucleotide sequence at positions 1081 to 1083 of the nucleotide sequence shown in SEQ ID NO: 2 by a codon encoding an amino acid residue different from a Ser residue, and encoding a polypeptide having GND activity.

The above DNAs of the present invention can be obtained by introducing a site-directed mutation into DNA encoding GND derived from a microorganism belonging to the genus *Corynebacterium*.

Examples of the microorganisms belonging to the genus *Corynebacterium* include those mentioned in the above (1).

An example of the DNA encoding GND derived from a microorganism belonging to the genus *Corynebacterium* is DNA having the nucleotide sequence shown in SEQ ID NO: 2 described in EP1108790.

The "region corresponding to the nucleotide sequence at positions 472 to 474 of the nucleotide sequence shown in SEQ ID NO: 2 in a nucleotide sequence of DNA encoding GND derived from a microorganism belonging to the *Corynebacterium*" refers to the region which corresponds to the nucleotide sequence at positions 472 to 474 of the nucleotide sequence shown in SEQ ID NO: 2 when the nucleotide sequence of DNA encoding GND derived from a microorganism belonging to the genus *Corynebacterium* and the nucleotide sequence shown in SEQ ID NO: 2 are compared and aligned in such a way that the homology between them becomes highest as calculated by use of BLAST, FASTA, etc. The region corresponding to the nucleotide sequence at positions 1081 to 1083 of the nucleotide sequence shown in SEQ ID NO: 2 can also be determined in the same manner.

The DNA having the nucleotide sequence shown in SEQ ID NO: 2 can be obtained by a conventional method such as PCR, based on the nucleotide sequence information described in EP1108790, from the chromosomal DNA derived from *Corynebacterium glutamicum* wild-type strain ATCC 13032 [method of Saito, et al., Biochim. Biophys. Acta, 72, 619 (1963)] or a cDNA library obtained by the following method. Other DNAs encoding GND derived from microorganisms belonging to the genus *Corynebacterium* can also be obtained by a conventional method such as PCR using the information on the nucleotide sequence shown in SEQ ID NO: 2.

The DNAs of the present invention can be obtained, for example, by introducing a site-directed mutation into the DNA having the nucleotide sequence shown in SEQ ID NO: 2 according to the description in Molecular Cloning, 3rd ed. or can be synthesized by a known method.

A cDNA library can be prepared by the methods described in Molecular Cloning, 3rd ed.; Current Protocols in Molecular Biology; DNA Cloning 1: Core Techniques, A Practical Approach, Second Edition, Oxford University Press (1995), etc. or methods using commercially available kits such as SuperScript Plasmid System for cDNA Synthesis and Plasmid Cloning (Gibco BRL) and ZAP-cDNA Synthesis Kit (Stratagene).

The cloning vector for preparing the cDNA library may be any phage vectors, plasmid vectors, etc. insofar as they can be autonomously replicated in *Escherichia coli* K12. Examples of suitable vectors include ZAP Express [Stratagene; Strategies, 5, 58 (1992)], pBluescript II SK(+) [Nucleic Acids Research, 17, 9494 (1989)], λzap II (Stratagene), λgt10, λgt11 [DNA Cloning, A Practical Approach, 1, 49 (1985)], λTriplEx (Clontech), λBlueMid (Clontech), λExCell (Pharmacia), pT7T318U (Pharmacia), pcD2 [Mol. Cell. Biol., 3, 280 (1983)] and pUC18 [Gene, 33, 103 (1985)].

As the microorganism for introducing the vector comprising the cDNA, any microorganism belonging to *Escherichia coli* can be used. Examples of suitable microorganisms are *Escherichia coli* XL1-Blue MRF' [Stratagene; Strategies, 5, 81 (1992)], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1966)] and *Escherichia coli* JM105 [Gene, 38, 275 (1985)].

The thus obtained DNAs of the present invention include DNA selected from the group consisting of DNAs according to the following (a-1) to (c-1):

(a-1) DNA having a nucleotide sequence wherein the nucleotide sequence shown in SEQ ID NO: 2 is modified by substitution of the region at positions 472 to 474 by a codon encoding an amino acid residue different from a Pro residue, and encoding a polypeptide having GND activity;

(b-1) DNA having a nucleotide sequence wherein the nucleotide sequence shown in SEQ ID NO: 2 is modified by substitution of the region at positions 1081 to 1083 by a codon encoding an amino acid residue different from a Ser residue, and encoding a polypeptide having GND activity; and (c-1) DNA having a nucleotide sequence wherein the nucleotide sequence shown in SEQ ID NO: 2 is modified by substitution of the region at positions 472 to 474 by a codon encoding an amino acid residue different from a Pro residue and substitution of the region at positions 1081 to 1083 by a codon encoding an amino acid residue different from a Ser residue, and encoding a polypeptide having GND activity.

Specific examples include DNA selected from the group consisting of DNAs according to the following (a-2) to (c-2):

(a-2) DNA having a nucleotide sequence wherein the nucleotide sequence shown in SEQ ID NO: 2 is modified by substitution of the cytosine residue at position 472 by a thymine residue;

(b-2) DNA having a nucleotide sequence wherein the nucleotide sequence shown in SEQ ID NO: 2 is modified by substitution of the cytosine residue at position 1082 by a thymine residue; and (c-2) DNA having a nucleotide sequence wherein the nucleotide sequence shown in SEQ ID NO: 2 is modified by substitution of the cytosine residue at position 472 by a thymine residue and substitution of the cytosine residue at position 1082 by a thymine residue.

The DNAs of the present invention further include DNAs according to the following (d) to (f) in addition to the DNAs according to the above (a) to (c), (a-1) to (c-1) and (a-2) to (c-2):

(d) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 472 to 474 of the nucleotide sequence shown in SEQ ID NO: 2 by a codon encoding an amino acid residue different from a Pro residue, having a codon encoding an amino acid residue different from a Pro residue at the region corresponding to said substituted region, and encoding a polypeptide having GND activity;

(e) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 1081 to 1083 of the nucleotide sequence shown in SEQ ID NO: 2 by a codon encoding an amino acid residue different from a Ser residue, having a codon encoding an amino acid residue different from a Ser residue at the region corresponding to said substituted region, and encoding a polypeptide having GND activity; and (f) DNA hybridizing with DNA having a nucleotide sequence complementary to a modified nucleotide sequence of DNA encoding GND derived from a microorganism belonging to the genus *Corynebacterium* under stringent conditions, said modification being substitution of the region corresponding to the nucleotide sequence at positions 472 to 474 of the nucleotide sequence shown in SEQ ID NO: 2 by a codon encoding an amino acid residue different from a Pro residue and substitution of the region corresponding to the nucleotide sequence at positions 1081 to 1083 of the nucleotide sequence shown in SEQ ID NO: 2 by a codon encoding an amino acid residue different from a Ser residue, having codons encoding an amino acid residue different from a Pro residue and an amino acid residue different from a Ser residue at the regions corresponding to said substituted regions, respectively, and encoding a polypeptide having GND activity.

The regions to be substituted can be determined by the same method as in the case of the DNAs of the above (a) to (c).

Examples of the microorganisms belonging to the genus *Corynebacterium* include those mentioned in the above (1).

The DNAs according to (d) to (f) can be obtained, for example, as DNAs which are capable of hybridizing with DNA having a nucleotide sequence complementary to the nucleotide sequence of the DNA according to any of the above (a-2) to (c-2) under stringent conditions and in which the region corresponding to the nucleotide sequence at positions 472 to 474 or the region corresponding to the nucleotide sequence at positions 1081 to 1083 is conserved as a codon encoding an amino acid residue different from a Pro residue or a codon encoding an amino acid residue different from a Ser residue, respectively.

The DNA capable of hybridizing with DNA having a nucleotide sequence complementary to the nucleotide sequence of the DNA according to any of (a-2) to (c-2) under stringent conditions refers to DNA obtained by colony hybridization, plaque hybridization, Southern blot hybridization, or the like using the DNA according to any of the above (a-2) to (c-2) as a probe. A specific example of such DNA is DNA which can be identified by carrying out hybridization at 65° C. in the presence of 0.7 to 1.0 mol/l sodium chloride using a filter with colony- or plaque-derived DNA immobilized thereon, and then washing the filter at 65° C. with a 0.1 to 2-fold conc. SSC solution (1-fold conc. SSC solution: 150 mmol/l sodium chloride and 15 mmol/l sodium citrate). Hybridization can be carried out according to the methods described in Molecular Cloning, 3rd ed.; Current Protocols in Molecular Biology; DNA Cloning 1: Core Techniques, A Practical Approach, Second Edition, Oxford University (1995), etc. Specifically, the DNA capable of hybridization includes DNA having at least 60% or more homology, preferably 80% or more homology, further preferably 95% or more homology to the nucleotide sequence of the DNA according to any of the above (a-2) to (c-2) as calculated by use of BLAST, FASTA, etc.

The amino acid residue different from a Pro residue encoded by the substituted region in the DNAs according to the above (a) to (f) may be any amino acid residue different from a Pro residue. Preferred amino acid residues are those having a neutral polar side chain such as Ser, Thr, Trp, Cys, Asn, Gln and Tyr. More preferred are those having a hydroxyl group on the side chain such as Ser and Thr, and a Ser residue is particularly preferred. The amino acid residue different from a Ser residue encoded by the substituted region may be any amino acid residue different from a Ser residue. Preferred amino acid residues are those having a nonpolar side chain such as Phe, Val, Leu, Ile, Met, Gly, Ala and Pro, and those having a ring-like structure on the side chain such as Phe and Trp. Particularly preferred is a Phe residue.

When DNA encoding GND derived from a microorganism belonging to the genus *Corynebacterium* has a nucleotide sequence wherein the region corresponding to positions 472 to 474 of the nucleotide sequence shown in SEQ ID NO: 2 is a codon encoding an amino acid residue different from a Pro residue and the region corresponding to positions 1081 to 1083 of the nucleotide sequence shown in SEQ ID NO: 2 is a codon encoding an amino acid residue different from a Ser residue, the substitution does not necessarily have to be carried out.

The above DNAs of the present invention are useful for the production of the polypeptides of the present invention and the production of L-amino acids.

(3) Production of the Polypeptide of the Present Invention

The polypeptides of the present invention of the above (1) can be produced by expressing the DNAs of the present invention of the above (2) in host cells using the methods described in Molecular Cloning, 3rd ed., Current Protocols in Molecular Biology, etc., for example, in the following manner.

DNA is prepared by replacing a nucleotide in the nucleotide sequence of the region encoding the polypeptide of the present invention so as to make a codon most suitable for the expression in a host cell. The DNA is useful for efficient production of the polypeptide of the present invention. This DNA fragment is inserted downstream of a promoter in an appropriate expression vector to prepare a recombinant vector. The recombinant vector is introduced into a host cell suited for the expression vector.

As the host cell, any bacterial cells or yeast cells that are capable of expressing the desired gene can be used. The expression vectors that can be employed are those capable of autonomous replication or integration into the chromosome in the above host cells and comprising a promoter at a position appropriate for the transcription of the DNA encoding the polypeptide of the present invention.

When a procaryote such as a bacterium is used as the host cell, it is preferred that the recombinant vector comprising the DNA encoding the polypeptide of the present invention is capable of autonomous replication in the procaryote and comprises a promoter, a ribosome binding sequence, the DNA of the present invention and a transcription termination sequence. The recombinant vector may further comprise a gene regulating the promoter.

Examples of suitable expression vectors are pBTrp2, pBTac1 and pBTac2 (all available from Boehringer Mannheim GmbH), pKK233-2 (Pharmacia), pSE280 (Invitrogen Corp.), pGEMEX-1 (Promega Corp.), pQE-8 (Qiagen, Inc.), pKYP10(Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(-) (Stratagene), pTrs30 [prepared from *Escherichia coli* JM109/pTrS30 (FERM BP-5407), pTrs32 [prepared from *Escherichia coil* JM109/pTrS32 (FERM BP-5408)], pGHA2 [prepared from *Escherichia coli* IGHA2 (FERM BP-400), Japanese Published Unexamined Patent Application No. 221091/85], pGKA2 [prepared from *Escherichia coil* IGKA2 (FERM BP-6798), Japanese Published Unexamined Patent Application No. 221091/85], pTerm2 (U.S. Pat. No. 4,686, 191, U.S. Pat. No. 4,939,094, U.S. Pat. No. 5,160,735), pSupex, pUB110, pTP5, pC194, pEG400 [J. Bacteriol., 172, 2392 (1990)], pGEX (Pharmacia) and pET system (Novagen, Inc.).

As the promoter, any promoters capable of functioning in host cells can be used. For example, promoters derived from *Escherichia coli* or phage, such as trp promoter ($P_{trp}$), lac promoter, $P_L$ promoter, $P_R$ promoter and T7 promoter can be used. Artificially designed and modified promoters such as a promoter in which two $P_{trp}$s are combined in tandem ($P_{trp}\times 2$), tac promoter, lacT7 promoter and letI promoter, etc. can also be used. It is preferred to use a plasmid in which the distance between the Shine-Dalgarno sequence (ribosome binding sequence) and the initiation codon is adjusted to an appropriate length (e.g., 6 to 18 bases). In the recombinant vector of the present invention, the transcription termination sequence is not essential for the expression of the DNA of the present invention, but it is preferred to place the transcription termination sequence immediately downstream of the structural gene.

Examples of suitable host cells include microorganisms belonging to the genera *Escherichia*, *Serratia*, *Bacillus*, *Brevibacterium*, *Corynebacterium*, *Microbacterium* and *Pseudomonas*. Specific examples are *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* GI698, *Escherichia coli* TB1, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Corynebacterium ammoniagenes* (former name: *Brevibacterium ammoniagenes*), *Corynebacterium flavum* ATCC 14067 (former name: *Brevibacterium flavum*), *Corynebacterium lactofermentum* ATCC 13869 (former name: *Brevibacterium lactofermentum*), *Corynebacterium glutamicum* ATCC 13032, *Corynebacterium glutamicum* ATCC 13869, *Corynebacterium acetoacidophilum* ATCC 13870, *Microbacterium* ammoniaphilum ATCC 15354, *Pseudomonas putida* and *Pseudomonas* sp. D-0110.

Among the microorganisms belonging to the genera *Corynebacterium*, *Brevibacterium* and *Microbacterium* used as host cells, preferred microorganisms are *Corynebacterium acetoacidophilum*, *Corynebacterium acetoglutamicum*, *Corynebacterium callunae*, *Corynebacterium glutamicum*, *Corynebacterium lactofermentum*, *Corynebacterium flavum*, *Corynebacterium herculis*, *Corynebacterium lilium*, *Corynebacterium melassecola*, *Corynebacterium thermoaminogenes*, *Corynebacterium efficiens*, *Corynebacterium ammoniagenes*, *Brevibacterium saccharolyticum*, *Brevibacterium immariophilum*, *Brevibacterium roseum*, *Brevibacterium thiogenitalis*, *Microbacterium ammoniaphilum*, etc.

More specifically, it is preferred to use *Corynebacterium acetoacidophilum* ATCC 13870, *Corynebacterium acetoglutamicum* ATCC 15806, *Corynebacterium* callunae ATCC 15991, *Corynebacterium* flavum ATCC 14067 (former name: *Brevibacterium flavum*), *Corynebacterium glutamicum* ATCC 13032, *Corynebacterium glutamicum* ATCC 13060, *Corynebacterium glutamicum* ATCC 13826 (former name: *Brevibacterium flavum*), *Corynebacterium glutamicum* ATCC 13869, *Corynebacterium glutamicum* ATCC 14020 (former name: *Brevibacterium divaricatum*), *Corynebacterium glutamicum* ATCC 13869 (former name: *Brevibacterium lactofermentum*), *Corynebacterium herculis* ATCC 13868, *Corynebacterium* lactofermentum ATCC 13869 (former name: *Brevibacterium lactofermentum*), *Corynebacterium lilium* ATCC 15990, *Corynebacterium melassecola* ATCC 17965, *Corynebacterium thermoaminogenes* ATCC 9244, *Corynebacterium thermoaminogenes* ATCC 9245, *Corynebacterium thermoaminogenes* ATCC 9246, *Corynebacterium thermoaminogenes* ATCC 9277, *Corynebacte-*

*rium ammoniagenes* ATCC 6871, *Corynebacterium ammoniagenes* ATCC 6872, *Brevibacterium saccharolyticum* ATCC 14066, *Brevibacterium immariophilum* ATCC 14068, *Brevibacterium roseum* ATCC 13825, *Brevibacterium thiogenitalis* ATCC 19240 and *Microbacterium ammoniaphilum* ATCC 15354.

When the host cell is the above microorganism belonging to the genus *Corynebacterium, Brevibacterium* or *Microbacterium*, it is preferred to use pCG1 (Japanese Published Unexamined Patent Application No. 134500/82), pCG2 (Japanese Published Unexamined Patent Application No. 35197/83), pCG4 (Japanese Published Unexamined Patent Application No. 183799/82), pCG11 (Japanese Published Unexamined Patent Application No. 134500/82), pCG116, pCE54 and pCB101 (Japanese Published Unexamined Patent Application No. 105999/83), pCE51, pCE52 and pCE53 [Molecular and General Genetics, 196, 175 (1984)], etc. as the vector for preparing a recombinant DNA comprising the DNA of the present invention.

Introduction of the recombinant vector can be carried out by any of the methods for introducing DNA into the above host cells, for example, the method using calcium ion [Proc. Natl. Acad. Sci. USA, 69,2110 (1972)], the protoplast method (e.g., Japanese Published Unexamined Patent Application No. 186492/82, the methods described in Gene, 17,107 (1982) and Molecular & General Genetics, 168, 111(1979), and electroporation [e.g., Journal of Bacteriology, 175, 4096 (1993)].

When yeast is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast strains can be used. Suitable promoters include promoters of genes of the glycolytic pathway such as hexokinase, PHO5 promoter, PGK promoter, GAP promoter, ADH promoter, gal 1 promoter, gal 10 promoter, heat shock polypeptide promoter, MFα1 promoter and CUP 1 promoter.

Examples of suitable host cells are microorganisms belonging to the genera *Saccharomyces, Schizosaccharomyces, Kluyveromyces, Trichosporon, Schwanniomyces, Pichia* and *Candida*, specifically, *Saccharomyces cerevisiae, Schizosaccharomyces pombe, Kluyveromyces lactis, Trichosporon pullulans, Schwanniomyces alluvius* and *Candida utilis*.

Introduction of the recombinant vector can be carried out by any of the methods for introducing DNA into yeast, for example, electroporation [Methods Enzymol., 194, 182 (1990)], the spheroplast method [Proc. Natl. Acad. Sci. USA, 75, 1929 (1978)], the lithium acetate method [J. Bacteriology, 153, 163 (1983)] and the method described in Proc. Natl. Acad. Sci. USA, 75, 1929 (1978).

When the DNA is expressed in yeast, a glycosylated polypeptide can be obtained.

Expression of the gene can be carried out not only by direct expression but also by secretory production, fusion protein expression, etc. according to the methods described in Molecular Cloning, 3rd ed., etc.

The polypeptide of the present invention can be produced by culturing the transformant obtained as above in a medium, allowing the polypeptide of the present invention to form and accumulate in the culture, and recovering the polypeptide from the culture.

Culturing of the transformant can be carried out by conventional culturing methods.

For the culturing of the transformant, any of natural media and synthetic media can be used insofar as it is a medium suitable for efficient culturing of the transformant which contains carbon sources, nitrogen sources, inorganic salts, etc. which can be assimilated by the transformant.

Examples of suitable carbon sources include carbohydrates such as glucose, fructose, sucrose, maltose and starch hydrolyzate, alcohols such as ethanol, and organic acids such as acetic acid, lactic acid and succinic acid.

As the nitrogen sources, ammonia, various organic or inorganic ammonium salts such as ammonium chloride, ammonium sulfate, ammonium carbonate and ammonium acetate, urea, and other nitrogen-containing compounds can be used as well as nitrogen-containing organic substances such as meat extract, yeast extract, corn steep liquor and soybean hydrolyzate.

Examples of the inorganic salts include potassium dihydrogenphosphate, dipotassium hydrogenphosphate, ammonium sulfate, sodium chloride, magnesium sulfate and calcium carbonate.

Additionally, micronutrients such as biotin and thiamine may be added according to need. These micronutrients can be substituted by medium additives such as meat extract, yeast extract, corn steep liquor and Casamino acid.

Culturing is carried out under aerobic conditions, for example, by shaking culture or submerged spinner culture under aeration. The culturing temperature is preferably 20 to 42° C., more preferably 30 to 40° C. The pH of the medium is preferably maintained at 5 to 9. The pH adjustment is carried out by using an organic or inorganic acid, an alkali solution, urea, calcium carbonate, ammonia, etc. Culturing is usually carried out for 1 to 6 days. If necessary, antibiotics such as ampicillin and tetracycline may be added to the medium during the culturing.

When a microorganism transformed with a recombinant vector comprising an inducible promoter is cultured, an inducer may be added to the medium, if necessary. For example, in the case of a microorganism transformed with a recombinant vector comprising lac promoter, isopropyl-β-D-thiogalactopyranoside or the like may be added to the medium; and in the case of a microorganism transformed with a recombinant vector comprising trp promoter, indoleacrylic acid or the like may be added.

Expression of the gene carrying the DNA of the present invention can be carried out not only by direct expression but also by secretory production, fusion polypeptide expression, etc. according to the methods described in Molecular Cloning, 3rd ed., etc.

The polypeptide of the present invention may be produced by intracellular production by host cells, extracellular secretion by host cells or production on outer membranes by host cells. A desirable production method can be adopted by changing the kind of the host cells used or the structure of the polypeptide to be produced.

When the polypeptide of the present invention is produced in host cells or on outer membranes of host cells, it is possible to have the polypeptide actively secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in Japanese Published Unexamined Patent Application No. 336963/93, WO94/23021, etc.

That is, the polypeptide of the present invention can be actively secreted outside the host cells by expressing it in the form of a protein in which a signal peptide is added upstream of a polypeptide containing the active site of the polypeptide of the present invention by the use of recombinant DNA techniques.

It is also possible to increase the polypeptide production by utilizing a gene amplification system using a dihydrofolate reductase gene or the like according to the method described in Japanese Published Unexamined Patent Application No. 227075/90.

Isolation and purification of the polypeptide produced by the transformant of the present invention can be carried out by conventional methods for isolating and purifying enzymes.

For example, when the polypeptide of the present invention is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract. A purified polypeptide preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the polypeptide is expressed as an inclusion body in cells, the cells are similarly recovered and disrupted, followed by centrifugation to recover the inclusion body of the polypeptide as a precipitate fraction. The recovered inclusion body of the polypeptide is solubilized with a protein-denaturing agent. The solubilized polypeptide solution is diluted or dialyzed to lower the concentration of the protein-denaturing agent in the solution, whereby the polypeptide is renatured to have normal higher-order structure. Then, a purified polypeptide preparation can be obtained by the same isolation and purification steps as described above.

When the polypeptide of the present invention or its derivative such as a glycosylated form is extracellularly secreted, the polypeptide or its derivative can be recovered in the culture supernatant. That is, the culture is treated by the same means as above, e.g., centrifugation, to obtain the culture supernatant. A purified polypeptide preparation can be obtained from the culture supernatant by using the same isolation and purification methods as described above.

An example of the polypeptides obtained in the above manner is a polypeptide selected from the group consisting of the polypeptides according to (a) to (f) in the above (1).

(4) Microorganisms Used for the Production of Useful Substances

The microorganisms to be used for the production of useful substances according to the present invention include the transformant obtained in the above (3) and a microorganism carrying the DNA of the present invention on the chromosome.

The microorganism carrying the DNA of the present invention on the chromosome can be obtained by introducing a site-directed mutation into the DNA mentioned in the above (2) which encodes GND on the chromosome of a microorganism used as the host cell of the transformant by conventional mutagenesis, gene replacement, cell fusion or transduction by recombinant DNA techniques, etc. Introduction of a site-directed mutation can be carried out according to the methods described in Molecular Cloning, 3rd ed.; Current Protocols in Molecular Biology; Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

The microorganism carrying the DNA of the present invention on the chromosome can also be prepared by replacing the DNA encoding GND on the chromosome by the DNA of the present invention obtained by the method of the above (2) by the use of the homologous recombination method.

Specifically, the DNA of the present invention obtained by the method of the above (2) is incorporated into a plasmid which can not replicate autonomously in host cells and which carries an antibiotic-resistance marker gene and the levansucrase gene of *Bacillus subtilis*, sacB [Mol. Microbiol., 6, 1195 (1992)], and the obtained plasmid is introduced into a microorganism according to the method described in the above (3).

As the recombinant plasmid can not replicate autonomously in the host cells, the transformant carrying the recombinant plasmid chromosomally integrated by Campbell-type homologous recombination can be selected based on the antibiotic resistance of the recombinant plasmid.

Then, a strain in which the DNA encoding GND on the chromosome of the host is replaced by the DNA of the present invention can be obtained by selection utilizing the suicide substrate-producing property of levansucrase of *Bacillus subtilis* integrated into the chromosome together with the DNA of the present invention [J. Bacteriol., 174, 5462 (1992)].

Gene replacement on the chromosome can be carried out as described above. In addition to the above method, any other methods for gene replacement capable of replacing genes on the chromosome can be employed.

Other methods for the preparation of the microorganism carrying the DNA of the present invention on the chromosome include cell fusion and transduction, for example, the method described in Hiroshi Aida, et al. (eds.), Amino Acid Fermentation, Gakkai Shuppan Center (1986).

(5) Production of Useful Substances

A useful substance can be produced by culturing the transformant obtained in the above (3) or the microorganism carrying the DNA of the present invention on the chromosome obtained in the above (4) in a medium, allowing the useful substance to form and accumulate in the culture, and recovering the useful substance from the culture.

Culturing of the transformant or the microorganism is carried out in the same manner as the culturing of the transformant described in the above (3).

After the culturing is completed, precipitates such as cells are removed from the obtained culture, and the useful substance can be recovered from the culture by combinations of known methods such as active carbon treatment and ion exchange resin treatment.

The useful substances include those obtained by biosynthesis, such as L-amino acids, nucleic acids or derivatives thereof, carbohydrates and vitamins, preferably, L-amino acids, or nucleic acids or derivatives thereof which are synthesized via the pentose phosphate cycle or which are biosynthesized using NADPH.

The substances which are synthesized via the pentose phosphate cycle include any substances synthesized via the pentose phosphate cycle, for example, L-amino acids biosynthesized via erythrose 4-phosphate on a metabolic pathway, such as L-tryptophan, L-phenylalanine and L-tyrosine, and nucleic acids or their derivatives biosynthesized via ribose 5-phosphate on a metabolic pathway, such as D-ribose, L-histidine, purine nucleotides, pyrimidine nucleotides, purine nucleosides, pyrimidine nucleosides, purine bases, pyrimidine bases and flavin nucleotides.

The substances biosynthesized using NADPH include any substances biosynthesized using NADPH. Examples of L-amino acids which require NADPH for biosynthesis are L-lysine, L-isoleucine, L-threonine and L-arginine. Examples of nucleic acids or their derivatives which require NADPH for biosynthesis are purine nucleotides and pyrimidine nucleotides.

Certain embodiments of the present invention are illustrated in the following examples. These examples are not to be construed as limiting the scope of the invention.

EXAMPLE 1

DNA encoding a polypeptide having an amino acid sequence wherein the Pro residue at position 158 of the amino acid sequence shown in SEQ ID NO: 1 was substituted by a Ser residue (Pro158Ser) was obtained by site-directed mutagenesis using PCR (Molecular Cloning, 3rd ed.) in the following manner.

The chromosomal DNA of the wild-type strain *Corynebacterium glutamicum* ATCC 13032 was prepared according to the method of Saito, et al. [Biochim. Biophys. Acta, 72, 619 (1963)].

Then, PCR was carried out using the chromosomal DNA as a template, Pfu turbo DNA polymerase (Stratagene) with the attached buffer, and the following primers. Based on the information on the nucleotide sequence of a known GND gene derived from *Corynebacterium glutamicum* (EP1108790), a DNA fragment consisting of the nucleotide sequence (SEQ ID NO: 4) wherein the region encoding the Pro residue (cca) at position 158 of the amino acid sequence of GND (SEQ ID NO: 1) was substituted by a codon encoding a Ser residue (tca) in the 21-nucleotide region containing the Pro residue-encoding region (positions 462 to 482) of SEQ ID NO: 2, which is the GND-encoding region of the GND gene, and a DNA fragment having the 21-nucleotide sequence shown in SEQ ID NO: 5, which is complementary to the sequence of SEQ ID NO: 4, were synthesized according to a conventional method, and were used as primers for PCR.

Separately, a DNA fragment consisting of the 14 5'-terminal nucleotides of the nucleotide sequence shown in SEQ ID NO: 2 and a nucleotide sequence upstream thereof was synthesized. The nucleotide sequence of the DNA fragment is shown in SEQ ID NO: 3.

A DNA fragment consisting of the nucleotide sequence complementary to the 20 3'-terminal nucleotides of the nucleotide sequence shown in SEQ ID NO: 2 and a nucleotide sequence downstream thereof was synthesized. The nucleotide sequence of the DNA fragment is shown in SEQ ID NO: 8.

Two kinds of PCR were carried out using the DNA fragments respectively having the nucleotide sequences shown in SEQ ID NOS: 3 and 5 and the DNA fragments respectively having the nucleotide sequences shown in SEQ ID NOS: 4 and 8 as respective primers, the obtained chromosomal DNA as a template, and Pfu turbo DNA polymerase (Stratagene) with the attached buffer.

The amplification products obtained by PCR (DNA fragments respectively corresponding to the nucleotide sequences at positions 1 to 482 and positions 462 to 1476 of the nucleotide sequence shown in SEQ ID NO: 2; ca. 0.5 kb and ca. 1.0 kb) were respectively separated by agarose gel electrophoresis, followed by extraction and purification using GENECLEAN Kit.

Then, PCR was carried out using the purified products as templates, and the DNA fragments respectively having the nucleotide sequences shown in SEQ ID NOS: 3 and 8 as primers. This PCR gave a ca. 1.5 kb DNA fragment wherein the region encoding the Pro residue at position 158 of the amino acid sequence of GND (cca) was substituted by a codon encoding Ser (tca). The obtained DNA fragment (ca. 1.5 kb) was separated by agarose gel electrophoresis, followed by extraction and purification using GENECLEAN Kit (BIO 101).

The DNA fragment was subjected to reaction in the presence of Taq polymerase (Boehringer Mannheim GmbH) and DATP at 72° C. for 10 minutes to add one adenine residue to the 3' end. The obtained DNA fragment (ca. 1.5 kb) was inserted into plasmid pESB30 by the TA cloning method (Molecular Cloning, 3rd ed.). pESB30 is a plasmid wherein a 2.6 kb PstI DNA fragment containing the levansucrase gene sacB derived from *Bacillus subtilis* [Mol. Microbiol., 6, 1195 (1992)] is ligated to the PstI cleavage site of vector pHSG299 carrying a kanamycin resistance gene [Gene, 61, 63 (1987)].

Specifically, pESB30 was cleaved with BamHI (Takara Shuzo Co., Ltd.) and subjected to agarose gel electrophoresis, and the pESB30 fragment was extracted and purified using GENECLEAN Kit (BIO 101). Both ends of the obtained pESB30 fragment were blunted using DNA Blunting Kit (Takara Shuzo Co., Ltd.) according to the attached protocol. The blunted pESB30 fragment was concentrated by phenol/chloroform extraction and ethanol precipitation, and then was subjected to reaction in the presence of Taq polymerase (Boehringer Mannheim GmbH) and dTTP at 70° C. for 2 hours for addition of one thymine nucleotide to the 3' end to prepare a pESB30-T fragment. The pESB30-T fragment and the above-obtained DNA fragment containing the added adenine nucleotide (ca. 1.5 kb) were mixed and subjected to ligase reaction using Ligation Kit ver. 1 (Takara Shuzo Co., Ltd.). Then, *Escherichia coli* DH5α (Toyobo Co., Ltd.) was transformed using the obtained reaction product according to a conventional method (Molecular Cloning, 3rd ed.).

The strain was cultured on LB agar medium [a medium comprising 10 g of Bacto-tryptone (Difco Laboratories Inc.), 5 g of yeast extract (Difco Laboratories Inc.), 10 g of sodium chloride and 16 g of Bacto-agar (Difco Laboratories Inc.) in 1 liter of water, pH 7.0] containing 20 µg/ml kanamycin to select a transformant. The transformant was cultured overnight in LB medium containing 20 µg/ml kanamycin, and a plasmid was prepared from the obtained culture according to the alkali SDS method (Molecular Cloning, 3rd ed.).

The plasmid was analyzed by cleavage with restriction enzymes, whereby it was confirmed that the plasmid had a structure wherein the above-obtained DNA fragment (ca. 1.5 kb) was inserted into pESB30. The plasmid was named pCgnd158.

EXAMPLE 2

DNA encoding a polypeptide having an amino acid sequence wherein the Ser residue at position 361 of the amino acid sequence shown in SEQ ID NO: 1 was substituted by a Phe residue (Ser361Phe) was obtained by site-directed mutagenesis using PCR in the same manner as in Example 1.

A DNA fragment consisting of the nucleotide sequence (SEQ ID NO: 6) wherein the region encoding the Ser residue (tcc) at position 361 of the amino acid sequence shown in SEQ ID NO: 1 was substituted by a codon encoding a Phe residue (ttc) in the 21-nucleotide region containing the Ser residue-encoding region (positions 1072 to 1092) of the nucleotide sequence shown in SEQ ID NO: 2, and a DNA fragment consisting of the 21-nucleotide sequence (SEQ ID NO: 7) which is complementary to the sequence of SEQ ID NO: 6 were synthesized. Two kinds of PCR were carried out using the DNA fragments respectively having the nucleotide sequences shown in SEQ ID NOS: 3 and 7 and the DNA fragments respectively having the nucleotide sequences shown in SEQ ID NOS: 6 and 8 as respective primers, the chromosomal DNA as a template, and Pfu turbo DNA polymerase with the attached buffer.

The amplification products obtained by PCR (DNA fragments respectively having the nucleotide sequences at positions 1 to 1092 and positions 1072 to 1476 of the nucleotide sequence shown in SEQ ID NO: 2; ca. 1.1 kb and ca. 0.4 kb) were respectively separated by agarose gel electrophoresis, followed by extraction and purification using GENECLEAN Kit.

Then, PCR was carried out using the purified products as templates, and the DNA fragments respectively having the nucleotide sequences shown in SEQ ID NOS: 3 and 8 as primers. This PCR gave a ca. 1.5 kb DNA fragment wherein the region encoding the Ser residue (tcc) at position 361 of the amino acid sequence of GND was substituted by a codon encoding a Phe residue (ttc). Then, the PCR product containing the obtained DNA fragment was subjected to reaction in the presence of Taq polymerase (Boehringer Mannheim GmbH) and DATP at 72° C. for 10 minutes to add one adenine nucleotide to the 3' end. The obtained DNA fragment (ca. 1.5 kb) was inserted into the plasmid pESB30-T in the same manner as in Example 1. The thus obtained plasmid was named pCgnd361.

EXAMPLE 3

DNA encoding a polypeptide having an amino acid sequence wherein the Pro residue at position 158 and the Ser residue at position 361 of the amino acid sequence shown in SEQ ID NO: 1 were respectively substituted by a Ser residue and a Phe residue was obtained by site-directed mutagenesis using PCR in the same manner as in Examples 1 and 2.

That is, two kinds of PCR were carried out using the DNA fragments respectively having the nucleotide sequences shown in SEQ ID NOS: 3 and 7 and the DNA fragments respectively having the nucleotide sequences shown in SEQ ID NOS: 6 and 8 as respective primers, the plasmid pCgnd158 prepared in Example 1 as a template, and Pfu turbo DNA polymerase with the attached buffer.

The amplification products obtained by PCR (DNA fragments respectively having the nucleotide sequences at positions 1 to 1092 and positions 1072 to 1476 of the nucleotide sequence shown in SEQ ID NO: 2; ca. 1.1 kb and ca. 0.4 kb) were respectively separated by agarose gel electrophoresis, followed by extraction and purification using GENECLEAN Kit.

Then, PCR was carried out using the purified products as templates, and the DNA fragments respectively having the nucleotide sequences shown in SEQ ID NOS: 3 and 8 as primers. This PCR gave a ca. 1.5 kb DNA fragment wherein the region encoding the Pro residue (cca) at position 158 and the region encoding the Ser residue (tcc) at position 361 of the amino acid sequence of GND were respectively substituted by a codon encoding a Ser residue (tca) and a codon encoding a Phe residue (ttc). Then, the PCR product containing the obtained DNA fragment was subjected to reaction in the presence of Taq polymerase (Boehringer Mannheim GmbH) and DATP at 72° C. for 10 minutes to add one adenine nucleotide to the 3' end. The obtained DNA fragment (ca. 1.5 kb) was inserted into the plasmid pESB30-T in the same manner as in Example 1. The thus obtained plasmid was named pCgndl536.

EXAMPLE 4

Introduction of Pro158Ser mutation, Ser361Phe mutation or both mutations into the GND gene of an L-lysine-producing strain was carried out by gene replacement using the above plasmids pCgnd158, pCgnd361 and pCgnd1536 prepared in Examples 1 to 3, respectively.

As the L-lysine-producing strain, *Corynebacterium glutamicum* strain AHP-3 (FERM BP-7382) whose genotype had been clarified was used. *Corynebacterium glutamicum* strain AHP-3 is a strain having amino acid substitution mutations Val59Ala, Thr331Ile and Pro458Ser respectively in the homoserine dehydrogenase gene (hom), the aspartokinase gene (lysC) and the pyruvate carboxylase gene (pyc) on the chromosome of the wild-type strain *Corynebacterium glutamicum* ATCC 13032.

Introduction of a mutation into the GND gene of the L-lysine-producing strain AHP-3 by gene replacement was carried out according to two recombination steps described below. By utilizing the incapability of the above plasmids (pCgnd158, pCgnd361 and pCgnd1536) to replicate autonomously in coryneform bacteria, strains prepared by integrating the respective plasmids into the chromosomal DNA of *Corynebacterium glutamicum* strain AHP-3 by homologous recombination were selected in the following manner.

Specifically, the AHP-3 strain was transformed with each of the plasmids by electroporation according to the method of Rest, et al. [Appl. Microbiol. Biotech., 52, 541 (1999)] to select kanamycin-resistant strains. The structure of the chromosome obtained from one of the selected kanamycin-resistant strains was examined by Southern hybridization (Molecular Cloning, 3rd ed.), whereby it was confirmed that the plasmid was integrated into the chromosome by Campbell-type homologous recombination. In such strains, the wild-type GND gene and the mutant GND gene exist close to each other on the chromosome and the second homologous recombination is apt to take place between them.

The above transformant (the primary recombinant) was spread on SUC agar medium [a medium comprising 100 g of sucrose, 7 g of meat extract, 10 g of peptone, 3 g of sodium chloride, 5 g of yeast extract (Difco Laboratories Inc.) and 18 g of Bacto-agar (Difco Laboratories Inc.) in 1 liter of water, pH 7.2] and cultured at 30° C. for one day to select a colony growing thereon. A strain carrying the sacB gene can not grow on this medium owing to the conversion of sucrose into a suicide substrate [J. Bacteriol., 174, 5462 (1991)]. On the contrary, a strain in which the second homologous recombination took place between the wild-type GND gene and the mutant GND gene existing close to each other on the chromosome becomes deficient in the sacB gene and can grow on this medium because a suicide substrate is not formed. At the second homologous recombination, either the wild-type gene or the mutant gene is deleted together with the sacB gene. Deletion of the wild-type gene together with the sacB gene means the gene replacement with the mutant gene.

The chromosomal DNA of the thus obtained secondary recombinant was prepared according to the method of Saito, et al. [Biochim. Biophys. Acta, 72, 619 (1963)]. PCR was carried out using this chromosomal DNA, the DNA fragments respectively having the nucleotide sequences shown in SEQ ID NOS: 3 and 8 as primers, and Pfu turbo DNA polymerase (Stratagene) with the attached buffer. The nucleotide sequence of the PCR product was determined by a conventional method to know whether the GND gene carried by the secondary recombinant was wild-type or mutant.

As a result, the following secondary recombinants having mutations in the GND gene were obtained: AGF-158 strain having Pro158Ser mutation, AGR-361 strain having Ser361Phe mutation, and APG-1536 strain having Pro158Ser and Ser361Phe mutations.

EXAMPLE 5

The obtained AGF-158 strain, AGR-361 strain and APG-1536 strain and their parent strain AHP-3 were separately cultured on BYG agar medium [a medium comprising 10 g of glucose, 7 g of meat extract, 10 g of peptone, 3 g of sodium chloride, 5 g of yeast extract (Difco Laboratories Inc.) and 18 g of Bacto-agar (Difco Laboratories Inc.) in 1 liter of water, pH 7.2] at 30° C. for 24 hours. Then, each of the strains was inoculated into a 2-liter Erlenmeyer flask with baffles containing 250 ml of a seed medium (a medium prepared by adding 30 g of calcium carbonate to a medium comprising 50 g of sucrose, 40 g of corn steep liquor, 8.3 g of ammonium sulfate, 1 g of urea, 2 g of potassium dihydrogenphosphate, 0.83 g of magnesium sulfate heptahydrate, 10 mg of iron sulfate heptahydrate, 1 mg of copper sulfate pentahydrate, 10 mg of zinc sulfate heptahydrate, 10 mg of β-alanine, 5 mg of nicotinic acid, 1.5 mg of thiamine hydrochloride and 0.5 mg of biotin in 1 liter of water, pH 7.2), followed by culturing at 30° C. for 12 to 16 hours.

The whole of each seed culture was inoculated into a 5-liter jar fermentor containing 1400 ml of a main culture medium (a medium comprising 60 g of glucose, 20 g of corn steep liquor, 25 g ammonium chloride, 2.5 g of potassium dihydrogenphosphate, 0.75 g of magnesium sulfate heptahydrate, 50 mg of iron sulfate heptahydrate, 13 mg of manganese sulfate pentahydrate, 50 mg of calcium chloride dihydrate, 6.3 mg of copper sulfate pentahydrate, 1.3 mg of zinc sulfate heptahydrate, 5 mg of nickel chloride hexahydrate, 1.3 mg of cobalt chloride hexahydrate, 1.3 mg of ammonium molybdate tetrahydrate, 14 mg of nicotinic acid, 23 mg of β-alanine, 7 mg of thiamine hydrochloride and 0.42 mg of biotin in 1 liter of water), followed by culturing at 1 vvm at 800 rpm at 34° C., during which the pH was kept at 7.0 with aqueous ammonia.

At the time when glucose in the medium was consumed, continuous addition of a glucose feeding solution (a medium comprising 400 g of glucose and 45 g of ammonium chloride in 1 liter of water) was started. The feeding solution was added at a flow rate adjusted so that it might be the same among the four strains. Culturing was terminated when the culturing time reached 28 hours.

After the cells were removed from the culture by centrifugation, the amount of L-lysine hydrochloride accumulated in the supernatant was determined by high performance liquid chromatography (HPLC). The results are shown in Table 1.

TABLE 1

| Strain | L-Lysine hydrochloride (g/l) |
| --- | --- |
| AHP-3 | 78 |
| AGF-158 | 81 |
| AGR-361 | 82 |
| APG-1536 | 84 |

As is clear from Table 1, the L-lysine productivity of the AGF-158 strain, AGR-361 strain and APG-1536 strain carrying the DNA of the present invention was apparently improved compared with that of the parent strain AHP-3.

EXAMPLE 6

Introduction of Pro158Ser mutation, Ser361Phe mutation or both mutations into the GND gene of *Corynebacterium glutamicum* ATCC 21660 (hereinafter referred to as ATCC 21660 strain) was carried out in the same manner as in Example 4 using pCgnd158, pCgnd361 and pCgnd1536 prepared in Examples 1 to 3, respectively.

*Corynebacterium glutamicum* ATCC 21660 is a mutant obtained from the wild-type strain *Corynebacterium glutamicum* ATCC 13032 by inducing methionine requirement mutation, α-amino-β-hydroxyvaleric acid (AHV) resistance mutation and S-(2-aminoethyl)-cysteine (AEC) resistance mutation [Agr. Biol. Chem., 36, 1611 (1972)].

As a result, the following secondary recombinants having mutations in the GND gene were obtained: THF-158 strain having Pro158Ser mutation, THR-361 strain having Ser361Phe mutation, and THG-1536 strain having Pro158Ser and Ser361Phe mutations.

EXAMPLE 7

The THF-158 strain, THR-361 strain and THG-1536 strain obtained in Example 6 and the ATCC 21660 strain were separately cultured on BYG agar medium at 30° C. for 24 hours. Then, each of the strains was inoculated into a test tube containing 10 ml of a seed medium (a medium comprising 20 g of glucose, 10 g of peptone, 10 g of yeast extract and 2.5 g of sodium chloride in 1 liter of water, pH 7.4), followed by culturing at 30° C. for 24 hours. Each seed culture (1 ml) was inoculated into a test tube containing 10 ml of a main culture medium (a medium prepared by adding 20 g of calcium carbonate to a medium comprising 100 g of glucose, 5 g of corn steep liquor, 20 g of ammonium sulfate, 0.5 g of dipotassium hydrogenphosphate, 0.5 g of potassium dihydrogenphosphate, 1 g of magnesium sulfate heptahydrate, 10 mg of iron sulfate heptahydrate, 10 mg of manganese sulfate pentahydrate, 0.1 mg of biotin and 0.1 mg of L-methionine in 1 liter of water, pH 7.4), followed by culturing at 30° C. for 72 hours.

After the cells were removed from the culture by centrifugation, the amount of L-threonine accumulated in the supernatant was determined by high performance liquid chromatography (HPLC). The results are shown in Table 2.

TABLE 2

| Strain | L-Threonine (g/l) |
| --- | --- |
| ATCC 21660 | 9.1 |
| THF-158 | 10 |
| THR-361 | 10.9 |
| THG-1536 | 11.3 |

As is clear from Table 2, the L-threonine productivity of the THF-158 strain, THR-361 strain and THG-1536 strain carrying the DNA of the present invention was apparently improved compared with that of the parent strain ATCC 21660.

EXAMPLE 8

Introduction of Pro158Ser mutation, Ser361Phe mutation or both mutations into the GND gene of *Corynebacterium glutamicum* FERM BP-986 (hereinafter referred to as FERM BP-986 strain) was carried out in the same manner as in Example 4 using pCgnd158, pCgnd361 and pCgnd1536 prepared in Examples 1 to 3, respectively.

*Corynebacterium glutamicum* FERM BP-986 is a mutant obtained from a wild-type strain of *Corynebacterium glutamicum* by inducing arginine requirement mutation, S-(2-aminoethyl)-cysteine resistance mutation, fluoropyruvic acid sensitivity mutation, rifampicillin resistance mutation and threonine hydroxamate resistance mutation (Japanese Published Unexamined Patent Application No. 195293/87).

As a result, the following secondary recombinants having mutations in the GND gene were obtained: ILF-158 strain having Pro158Ser mutation, ILR-361 strain having Ser361Phe mutation, and ILG-1536 strain having Pro158Ser and Ser361Phe mutations.

EXAMPLE 9

The ILF-158 strain, ILR-361 strain and ILG-1536 strain obtained in Example 8 and the FERM BP-986 strain were separately cultured on BYG agar medium at 28° for 24 hours. Then, each of the strains was inoculated into a 300- ml Erlenmeyer flask containing 20 ml of a seed medium [a medium comprising 50 g of glucose, 10 g of yeast extract (Difco Laboratories Inc.), 10 g of peptone, 3 g of urea, 2.5 g of sodium chloride, 5 g of corn steep liquor and 50 µg of biotin in 1 liter of water, pH 7.2], followed by shaking culture at 28° for 24 hours. Each seed culture (2 ml) was inoculated into a 300-ml Erlenmeyer flask containing 20 ml of a main culture medium [a medium comprising 70 g of molasses (calculated in terms of glucose), 5 g of corn steep liquor, 20 g of ammonium chloride, 2 g of urea, 2 g of potassium dihydrogenphosphate, 0.5 g of magnesium sulfate heptahydrate, 0.01 g of iron sulfate heptahydrate, 0.01 g of manganese chloride tetrahydrate, 0.01 g of copper sulfate pentahydrate, 0.01 g of calcium chloride dihydrate, 1 mg of zinc sulfate heptahydrate, 1 mg of nickel chloride, 1 mg of ammonium molybdate tetrahydrate, 1 mg of cobalt chloride hexahydrate, 10 mg of calcium pantothenate, 1 mg of nicotinic acid, 50 µg of biotin and 0.5 g of arginine hydrochloride in 1 liter of water, pH 7.4], followed by culturing in the same manner as in the seed culture for 72 hours.

After the cells were removed from the culture by centrifugation, the amount of L-isoleucine accumulated in the supernatant was determined by high performance liquid chromatography (HPLC). The results are shown in Table 3.

TABLE 3

| Strain | L-Isoleucine (g/l) |
|---|---|
| FERM BP-986 | 13 |
| ILF-158 | 13.6 |
| ILR-361 | 14 |
| ILG-1536 | 14.4 |

As is clear from Table 3, the L-isoleucine productivity of the ILF-158 strain, ILR-361 strain and ILG-1536 strain carrying the DNA of the present invention was significantly improved compared with that of the parent strain FERM BP-986.

EXAMPLE 10

Introduction of Pro158Ser mutation, Ser361Phe mutation or both mutations into the GND gene of *Corynebacterium glutamicum* KY10671 (FERM P-3616) (hereinafter referred to as KY10671 strain) was carried out in the same manner as in Example 4 using pCgnd158, pCgnd361 and pCgnd1536 prepared in Examples 1 to 3, respectively.

The KY10671 strain is a mutant obtained from a wild-type strain of *Corynebacterium glutamicum* by inducing D-serine sensitivity mutation, D-arginine resistance mutation, arginine hydroxamate resistance mutation and 6-azauracil resistance mutation (Japanese Published Unexamined Patent Application Nos. 12491/78 and 257486/89).

As a result, the following secondary recombinants having mutations in the GND gene were obtained: ARF-158 strain having Pro158Ser mutation, ARR-361 strain having Ser361Phe mutation, and ARG-1536 strain having Pro158Ser and Ser361Phe mutations.

EXAMPLE 11

The ARF-158 strain, ARR-361 strain, ARG-1536 strain and KY10671 strain were separately cultured on BYG agar medium at 30° C. for 24 hours. Then, each of the strains was inoculated into a test tube containing 6 ml of a seed medium (a medium comprising 20 g of glucose, 10 g of peptone, 10 g of yeast extract and 2.5 g of sodium chloride in 1 liter of water, pH 7.2), followed by culturing at 30° C. for 24 hours. Each seed culture (2 ml) was inoculated into a 300-ml Erlenmeyer flask containing 20 ml of a main culture medium [a medium prepared by adding 30 g of calcium carbonate to a medium comprising 150 g of molasses (calculated in terms of glucose), 5 g of corn steep liquor, 30 g of ammonium sulfate, 3 g of urea, 0.5 g of dipotassium hydrogenphosphate, 0.5 g of potassium dihydrogenphosphate and 0.25 g of magnesium sulfate dihydrate in 1 liter of water, pH 7.2], followed by culturing at 30° C. for 72 hours.

After the cells were removed from the culture by centrifugation, the amount of L-arginine accumulated in the supernatant was determined by high performance liquid chromatography (HPLC). The results are shown in Table 4.

TABLE 4

| Strain | L-Arginine (g/l) |
|---|---|
| KY10671 | 22 |
| ARF-158 | 23.2 |
| ARR-361 | 23.9 |
| ARG-1536 | 24.8 |

As is clear from Table 4, the L-arginine productivity of the ARF-158 strain, ARR-361 strain and ARG-1536 strain carrying the DNA of the present invention was apparently improved compared with that of the parent strain KY10671.

EXAMPLE 12

Introduction of Pro158Ser mutation, Ser361Phe mutation or both mutations into the GND gene of *Corynebacterium glutamicum* BPS-13 (FERM BP-1777) (hereinafter referred to as FERM BP-1777 strain) was carried out in the same manner as in Example 4 using pCgnd158, pCgnd361 and pCgnd1536 prepared in Examples 1 to 3, respectively.

The FERM BP-1777 strain is a mutant obtained from a wild-type strain of *Corynebacterium glutamicum* by inducing L-phenylalanine and L-tyrosine requirement mutations, mutations conferring resistance to various aromatic amino acid analogues and 3-bromopyruvic acid sensitivity mutation (Japanese Patent No. 2578488).

As a result, the following secondary recombinants having mutations in the GND gene were obtained: TRF-158 strain having Pro158Ser mutation, TRR-361 strain having Ser361Phe mutation, and TRG-1536 strain having Pro158Ser and Ser361Phe mutations.

EXAMPLE 13

The TRF-158 strain, TRR-361 strain, TRG-1536 strain and FERM BP-1777 strain were separately cultured on BYG agar medium at 30° C. for 24 hours. Then, each of the strains was inoculated into a test tube containing 6 ml of a seed medium (a medium comprising 20 g of glucose, 15 g of polypeptone, 15 g of yeast extract, 2.5 g of sodium chloride, 1 g of urea, 200 mg of L-phenylalanine and 200 mg of L-tyrosine in 1 liter of water, pH 7.2), followed by culturing at 30° C. for 24 hours. Each seed culture (2 ml) was inoculated into a 300-ml Erlenmeyer flask containing 20 ml of a main culture medium (a medium prepared by adding 20 g of calcium carbonate to a medium comprising 60 g of glucose, 10 g of corn steep liquor, 20 g of ammonium sulfate, 0.5 g of dipotassium hydrogenphosphate, 0.5 g of potassium dihydrogenphosphate, 0.25 g of magnesium sulfate heptahydrate, 10 mg of manganese sulfate heptahydrate and 0.03 g of biotin in 1 liter of water, pH 7.2), followed by culturing at 30° C. for 72 hours.

After the cells were removed from the culture by centrifugation, the amount of L-tryptophan accumulated in the supernatant was determined by high performance liquid chromatography (HPLC). The results are shown in Table 5.

TABLE 5

| Strain | L-Tryptophan (g/l) |
|---|---|
| FERM BP-1777 | 7.5 |
| TRF-158 | 8 |
| TRR-361 | 8.3 |
| TRG-1536 | 8.7 |

As is clear from Table 5, the L-tryptophan productivity of the TRF-158 strain, TRR-361 strain and TRG-1536 strain carrying the DNA of the present invention was apparently improved compared with that of the parent strain FERM BP-1777.

TEST EXAMPLE 1

Measurement of GND Activity

The GND activity of the above AGF-158 strain, AGR-361 strain and APG-1536 strain obtained in Example 4 and their parent strain AHP-3 was measured according to the method described in Agric. Biol. Chem., 51, 1257 (1987) and Enzme Microb Technol., 28, 754 (2001) in the following manner.

*Corynebacterium glutamicum* AHP-3 carries no mutation associated with GND activity and the GND activity of the strain is equal to that of *Corynebacterium glutamicum* ATCC 13032.

The ATCC 13032 strain, AHP-3 strain, AGF-158 strain, AGR-361 strain and APG-1536 strain were separately inoculated into 200 ml of MMYE medium [a medium comprising 20 g of glucose, 10 g of ammonium sulfate, 3 g of urea, 1 g of potassium dihydrogenphosphate, 0.4 g of magnesium sulfate heptahydrate, 50 mg of sodium chloride, 2 mg of iron sulfate heptahydrate, 2 mg of manganese sulfate pentahydrate, 0.2 mg of thiamine hydrochloride, 0.05 mg of biotin and 1 g of yeast extract (Difco Laboratories Inc.) in 1 liter of water, pH 7.2], followed by culturing at 30° C.

During the culturing, the turbidity of the culture was measured with a spectrophotometer, and the culturing was terminated when the OD 660 nm of the culture reached 7 to 8. After the termination of the culturing, the culture was centrifuged at 4000 g at 4° C. for 10 minutes. The obtained cells were washed twice with an ice-cooled lysis buffer [comprising 50 mmol/l Tris/HCl (pH 7.5), 500 mmol/l potassium chloride, 2 mmol/l 2-mercaptoethanol and 5% glycerol]. After washing, 10 ml of a lysis buffer was added to suspend the cells therein.

The cells in the suspension were disrupted by using a sonicator. The suspension containing the disrupted cells was centrifuged at 4° C. for 30 minutes, and the obtained supernatant was suspended in a lysis buffer at a final protein concentration of 5 to 15 mg/ml to prepare a crude enzyme solution.

The crude enzyme solution was added to a reaction mixture comprising 50 mmol/l Tris/HCl (pH 7.5), 0.5 mmol/l NADP, 10 mmol/l magnesium chloride and 2 mmol/l 6-phosphogluconic acid to make up to 1.5 ml. The resulting mixture was subjected to reaction in a 1-ml cuvette at 30° C. and the increase in the absorbance was measured at 340 nm. On the basis of the molar extinction coefficient of NADPH (6220), the amount of NADPH formed per minute was calculated. GND specific activity was expressed in terms of the amount of NADPH formed per mg of protein per minute.

The GND specific activity of the ATCC 13032 strain, AHP-3 strain, AGF-158 strain, AGR-361 strain and APG-1536 strain is shown in Table 6.

TABLE 6

| Strain | GND specific activity (nmol/min/mg of protein) |
|---|---|
| ATCC 13032 | 74 |
| AHP-3 | 76 |
| AGF-158 | 75 |
| AGR-361 | 33 |
| APG-1536 | 34 |

INDUSTRIAL APPLICABILITY

The present invention provides modified GND and DNA encoding the GND. The use of the modified GND enhances the efficiency in the production of useful substances by microorganisms.

[Sequence Listing Free Text]

| SEQ ID NO: 3 | Description of artificial sequence: synthetic DNA |
| SEQ ID NO: 4 | Description of artificial sequence: synthetic DNA |
| SEQ ID NO: 5 | Description of artificial sequence: synthetic DNA |
| SEQ ID NO: 6 | Description of artificial sequence: synthetic DNA |
| SEQ ID NO: 7 | Description of artificial sequence: synthetic DNA |
| SEQ ID NO: 8 | Description of artificial sequence: synthetic DNA |

The invention claimed is:

1. An isolated polypeptide having a 95% or more homology to the amino acid sequence of SEQ ID NO: 1 and substitution of the amino acid residue at the position corresponding to the 158th amino acid of the amino acid sequence of SEQ ID NO: 1 by an amino acid residue selected from the group consisting of Ser, Thr, Trp, Cys, Asn, Gln and Tyr, and having GND activity.

2. An isolated polypeptide having a 95% or more homology to the amino acid sequence of SEQ ID NO: 1, substitution of the amino acid residue at the position corresponding to the 158th amino acid of the amino acid sequence of SEQ ID NO: 1 by an amino acid residue selected from the group consisting of Ser, Thr, Trp, Cys, Asn, Gln and Tyr and substitution of the amino acid residue at the position corresponding to the 361st amino acid of the amino acid sequence of SEQ ID NO: 1 by an amino acid residue selected from the group consisting of Phe, Val, Leu, Ile, Met, Gly, Ala, Pro and Trp, and having GND activity.

3. An isolated polypeptide selected from the group consisting of polypeptides according to the following (a) and (b):
   (a) an isolated polypeptide having a modified amino acid sequence of 6-phosphogluconate dehydrogenase (hereinafter abbreviated as GND) isolated from a microorganism belonging to the genus *Corynebacterium*, said modification consisting of substitution of the amino acid residue at the position corresponding to the 158th amino acid of the amino acid sequence of SEQ ID NO: 1 by an amino acid residue selected from the group consisting of Ser, Thr, Trp, Cys, Asn, Gln and Tyr, and having GND activity; and
   (b) an isolated polypeptide having a modified amino acid sequence of GND isolated from a microorganism belonging to the genus *Corynebacterium*, said modification consisting of substitution of the amino acid residue at the position corresponding to the 158th amino acid of the amino acid sequence of SEQ ID NO: 1 by an amino acid residue selected from the group consisting of Ser, Thr, Trp, Cys, Asn, Gln and Tyr and substitution of the amino acid residue at the position corresponding to the 361st amino acid of the amino acid sequence of SEQ ID NO: 1 by an amino acid residue selected from the group consisting of Phe, Val, Leu, Ile, Met, Gly, Ala, Pro and Trp, and having GND activity,
   wherein the GND isolated from the microorganism belonging to the genus *Corynebacterium* is GND having the amino acid sequence of SEQ ID NO: 1.

4. The isolated polypeptide according to claim 3, wherein the amino acid residue selected from the group consisting of Ser, Thr, Trp, Cys, Asn, Gln and Tyr is a Ser residue.

5. The isolated polypeptide according to claim 3, wherein the amino acid residue selected from the group consisting of Ser, Thr, Trp, Cys, Asn, Gln and Tyr is a Ser residue and the amino acid residue selected from the group consisting of Phe, Val, Leu, Ile, Met, Gly, Ala, Pro and Trp is a Phe residue.

* * * * *

SEQUENCE LISTING

<160> NUMBER OF SEQ ID NOS: 8

<210> SEQ ID NO 1
<211> LENGTH: 492

<212> TYPE: PRT
<213> ORGANISM: Corynebacterium glutamicum ATCC13032

<400> SEQUENCE: 1

```
Met Pro Ser Ser Thr Ile Asn Asn Met Thr Asn Gly Asp Asn Leu Ala
 1               5                  10                  15

Gln Ile Gly Val Val Gly Leu Ala Val Met Gly Ser Asn Leu Ala Arg
            20                  25                  30

Asn Phe Ala Arg Asn Gly Asn Thr Val Ala Val Tyr Asn Arg Ser Thr
        35                  40                  45

Asp Lys Thr Asp Lys Leu Ile Ala Asp His Ser Glu Gly Asn Phe
     50                  55                  60

Ile Pro Ser Ala Thr Val Glu Glu Phe Val Ala Ser Leu Glu Lys Pro
 65                  70                  75                  80

Arg Arg Ala Ile Ile Met Val Gln Ala Gly Asn Ala Thr Asp Ala Val
                85                  90                  95

Ile Asn Gln Leu Ala Asp Ala Met Asp Glu Gly Asp Ile Ile Ile Asp
            100                 105                 110

Gly Gly Asn Ala Leu Tyr Thr Asp Thr Ile Arg Arg Glu Lys Glu Ile
        115                 120                 125

Ser Ala Arg Gly Leu His Phe Val Gly Ala Gly Ile Ser Gly Gly Glu
    130                 135                 140

Glu Gly Ala Leu Asn Gly Pro Ser Ile Met Pro Gly Gly Pro Ala Lys
145                 150                 155                 160

Ser Tyr Glu Ser Leu Gly Pro Leu Leu Glu Ser Ile Ala Ala Asn Val
                165                 170                 175

Asp Gly Thr Pro Cys Val Thr His Ile Gly Pro Asp Gly Ala Gly His
            180                 185                 190

Phe Val Lys Met Val His Asn Gly Ile Glu Tyr Ala Asp Met Gln Val
        195                 200                 205

Ile Gly Glu Ala Tyr His Leu Leu Arg Tyr Ala Ala Gly Met Gln Pro
    210                 215                 220

Ala Glu Ile Ala Glu Val Phe Lys Glu Trp Asn Ala Gly Asp Leu Asp
225                 230                 235                 240

Ser Tyr Leu Ile Glu Ile Thr Ala Glu Val Leu Ser Gln Val Asp Ala
                245                 250                 255

Glu Thr Gly Lys Pro Leu Ile Asp Val Ile Val Asp Ala Ala Gly Gln
            260                 265                 270

Lys Gly Thr Gly Arg Trp Thr Val Lys Ala Ala Leu Asp Leu Gly Ile
        275                 280                 285

Ala Thr Thr Gly Ile Gly Glu Ala Val Phe Ala Arg Ala Leu Ser Gly
    290                 295                 300

Ala Thr Ser Gln Arg Ala Ala Ala Gln Gly Asn Leu Pro Ala Gly Val
305                 310                 315                 320

Leu Thr Asp Leu Glu Ala Leu Gly Val Asp Lys Ala Gln Phe Val Glu
                325                 330                 335

Asp Val Arg Arg Ala Leu Tyr Ala Ser Lys Leu Val Ala Tyr Ala Gln
            340                 345                 350

Gly Phe Asp Glu Ile Lys Ala Gly Ser Asp Glu Asn Asn Trp Asp Val
        355                 360                 365

Asp Pro Arg Asp Leu Ala Thr Ile Trp Arg Gly Gly Cys Ile Ile Arg
    370                 375                 380
```

```
Ala Lys Phe Leu Asn Arg Ile Val Glu Ala Tyr Asp Ala Asn Ala Glu
385                 390                 395                 400

Leu Glu Ser Leu Leu Leu Asp Pro Tyr Phe Lys Ser Glu Leu Gly Asp
            405                 410                 415

Leu Ile Asp Ser Trp Arg Arg Val Ile Val Thr Ala Thr Gln Leu Gly
                420                 425                 430

Leu Pro Ile Pro Val Phe Ala Ser Ser Leu Ser Tyr Tyr Asp Ser Leu
            435                 440                 445

Arg Ala Glu Arg Leu Pro Ala Ala Leu Ile Gln Gly Gln Arg Asp Phe
    450                 455                 460

Phe Gly Ala His Thr Tyr Lys Arg Ile Asp Lys Asp Gly Ser Phe His
465                 470                 475                 480

Thr Glu Trp Ser Gly Asp Arg Ser Glu Val Glu Ala
                485                 490

<210> SEQ ID NO 2
<211> LENGTH: 1476
<212> TYPE: DNA
<213> ORGANISM: Corynebacterium glutamicum ATCC13032

<400> SEQUENCE: 2 atg ccg tca agt acg atc aat aac atg act aat gga gat aat ctc gca        48
Met Pro Ser Ser Thr Ile Asn Asn Met Thr Asn Gly Asp Asn Leu Ala
1               5                   10                  15 cag atc ggc gtt gta ggc cta gca gta atg ggc tca aac ctc gcc cgc        96
Gln Ile Gly Val Val Gly Leu Ala Val Met Gly Ser Asn Leu Ala Arg
            20                  25                  30 aac ttc gcc cgc aac ggc aac act gtc gct gtc tac aac cgc agc act       144
Asn Phe Ala Arg Asn Gly Asn Thr Val Ala Val Tyr Asn Arg Ser Thr
        35                  40                  45 gac aaa acc gac aag ctc atc gcc gat cac ggc tcc gaa ggc aac ttc       192
Asp Lys Thr Asp Lys Leu Ile Ala Asp His Gly Ser Glu Gly Asn Phe
    50                  55                  60 atc cct tct gca acc gtc gaa gag ttc gta gca tcc ctg gaa aag cca       240
Ile Pro Ser Ala Thr Val Glu Glu Phe Val Ala Ser Leu Glu Lys Pro
65                  70                  75                  80 cgc cgc gcc atc atc atg gtt cag gct ggt aac gcc acc gac gca gtc       288
Arg Arg Ala Ile Ile Met Val Gln Ala Gly Asn Ala Thr Asp Ala Val
                85                  90                  95 atc aac cag ctg gca gat gcc atg gac gaa ggc gac atc atc atc gac       336
Ile Asn Gln Leu Ala Asp Ala Met Asp Glu Gly Asp Ile Ile Ile Asp
            100                 105                 110 ggc ggc aac gcc ctc tac acc gac acc att cgt cgc gag aag gaa atc       384
Gly Gly Asn Ala Leu Tyr Thr Asp Thr Ile Arg Arg Glu Lys Glu Ile
        115                 120                 125 tcc gca cgc ggt ctc cac ttc gtc ggt gct ggt atc tcc ggc ggc gaa       432
Ser Ala Arg Gly Leu His Phe Val Gly Ala Gly Ile Ser Gly Gly Glu
    130                 135                 140 gaa ggc gca ctc aac ggc cca tcc atc atg cct ggt ggc cca gca aag       480
Glu Gly Ala Leu Asn Gly Pro Ser Ile Met Pro Gly Gly Pro Ala Lys
145                 150                 155                 160 tcc tac gag tcc ctc gga cca ctg ctt gag tcc atc gct gcc aac gtt       528
Ser Tyr Glu Ser Leu Gly Pro Leu Leu Glu Ser Ile Ala Ala Asn Val
                165                 170                 175 gac ggc acc cca tgt gtc acc cac atc ggc cca gac ggc gcc ggc cac       576
Asp Gly Thr Pro Cys Val Thr His Ile Gly Pro Asp Gly Ala Gly His
            180                 185                 190
```

```
ttc gtc aag atg gtc cac aac ggc atc gag tac gcc gac atg cag gtc      624
Phe Val Lys Met Val His Asn Gly Ile Glu Tyr Ala Asp Met Gln Val
        195                 200                 205 atc ggc gag gca tac cac ctt ctc cgc tac gca gca ggc atg cag cca      672
Ile Gly Glu Ala Tyr His Leu Leu Arg Tyr Ala Ala Gly Met Gln Pro
    210                 215                 220 gct gaa atc gct gag gtt ttc aag gaa tgg aac gca ggc gac ctg gat      720
Ala Glu Ile Ala Glu Val Phe Lys Glu Trp Asn Ala Gly Asp Leu Asp
225                 230                 235                 240 tcc tac ctc atc gaa atc acc gca gag gtt ctc tcc cag gtg gat gct      768
Ser Tyr Leu Ile Glu Ile Thr Ala Glu Val Leu Ser Gln Val Asp Ala
            245                 250                 255 gaa acc ggc aag cca cta atc gac gtc atc gtt gac gct gca ggt cag      816
Glu Thr Gly Lys Pro Leu Ile Asp Val Ile Val Asp Ala Ala Gly Gln
                260                 265                 270 aag ggc acc gga cgt tgg acc gtc aag gct gct ctt gat ctg ggt att      864
Lys Gly Thr Gly Arg Trp Thr Val Lys Ala Ala Leu Asp Leu Gly Ile
        275                 280                 285 gct acc acc ggc atc ggc gaa gct gtt ttc gca cgt gca ctc tcc ggc      912
Ala Thr Thr Gly Ile Gly Glu Ala Val Phe Ala Arg Ala Leu Ser Gly
    290                 295                 300 gca acc agc cag cgc gct gca cag ggc aac cta cct gca ggt gtc          960
Ala Thr Ser Gln Arg Ala Ala Gln Gly Asn Leu Pro Ala Gly Val
305                 310                 315                 320 ctc acc gat ctg gaa gca ctt ggc gtg gac aag gca cag ttc gtc gaa     1008
Leu Thr Asp Leu Glu Ala Leu Gly Val Asp Lys Ala Gln Phe Val Glu
            325                 330                 335 gac gtt cgc cgt gca ctg tac gca tcc aag ctt gtt gct tac gca cag     1056
Asp Val Arg Arg Ala Leu Tyr Ala Ser Lys Leu Val Ala Tyr Ala Gln
                340                 345                 350 ggc ttc gac gag atc aag gct ggc tcc gac gag aac aac tgg gac gtt     1104
Gly Phe Asp Glu Ile Lys Ala Gly Ser Asp Glu Asn Asn Trp Asp Val
        355                 360                 365 gac cct cgc gac ctc gct acc atc tgg cgc ggc ggc tgc atc att cgc     1152
Asp Pro Arg Asp Leu Ala Thr Ile Trp Arg Gly Gly Cys Ile Ile Arg
    370                 375                 380 gct aag ttc ctc aac cgc atc gtc gaa gca tac gat gca aac gct gaa     1200
Ala Lys Phe Leu Asn Arg Ile Val Glu Ala Tyr Asp Ala Asn Ala Glu
385                 390                 395                 400 ctt gag tcc ctg ctg ctc gat cct tac ttc aag agc gag ctc ggc gac     1248
Leu Glu Ser Leu Leu Leu Asp Pro Tyr Phe Lys Ser Glu Leu Gly Asp
            405                 410                 415 ctc atc gat tca tgg cgt cgc gtg att gtc acc gcc acc cag ctt ggc     1296
Leu Ile Asp Ser Trp Arg Arg Val Ile Val Thr Ala Thr Gln Leu Gly
                420                 425                 430 ctg cca atc cca gtg ttc gct tcc tcc ctg tcc tac tac gac agc ctg     1344
Leu Pro Ile Pro Val Phe Ala Ser Ser Leu Ser Tyr Tyr Asp Ser Leu
        435                 440                 445 cgt gca gag cgt ctg cca gca gcc ctg atc caa gga cag cgc gac ttc     1392
Arg Ala Glu Arg Leu Pro Ala Ala Leu Ile Gln Gly Gln Arg Asp Phe
    450                 455                 460 ttc ggt gcg cac acc tac aag cgc atc gac aag gat ggc tcc ttc cac     1440
Phe Gly Ala His Thr Tyr Lys Arg Ile Asp Lys Asp Gly Ser Phe His
465                 470                 475                 480 acc gag tgg tcc ggc gac cgc tcc gag gtt gaa gct                     1476
Thr Glu Trp Ser Gly Asp Arg Ser Glu Val Glu Ala
            485                 490
```

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
caccgggcta tgccgtcaag tac                                           23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
gcctggtggc tcagcaaagt c                                             21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gactttgctg agccaccagg c                                             21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
aaggctggct tcgacgagaa c                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gttctcgtcg aagccagcct t                                             21

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ttaagcttca acctcggagc ggt                                           23